United States Patent [19]

Verga et al.

[11] Patent Number: 4,652,654
[45] Date of Patent: Mar. 24, 1987

[54] PROCESS FOR PREPARING 2(4-FLUOROPHENYL)ALPHA-METHYL-5-BENZOXAZOLE ACETIC ACID

[75] Inventors: Alberto Verga; Roberto Signorini, both of Milan, Italy

[73] Assignee: Ravizza Spa, Muggio, Italy

[21] Appl. No.: 784,892

[22] Filed: Oct. 7, 1985

[30] Foreign Application Priority Data

Oct. 22, 1984 [IT] Italy .............................. 23264 A/84

[51] Int. Cl.$^4$ ......................................... C07D 263/56
[52] U.S. Cl. .................................................. 548/217
[58] Field of Search ........................................ 548/217

[56] References Cited

U.S. PATENT DOCUMENTS

| | | | |
|---|---|---|---|
| 3,912,748 | 10/1975 | Evans et al. | 548/217 |
| 3,962,452 | 6/1976 | Evans et al. | 514/375 |
| 4,025,636 | 5/1977 | Dunwell et al. | 514/375 |

OTHER PUBLICATIONS

Ambros et al., Chem. Abst. 99-70710z.
Botija Menchero et al., Chem. Abst. 104-88520u.
Signorini et al., Chem. Abst. 100-209792n.
Cockerill et al., Chem. Abst. 86-139910r.
Evans, Chem. Abst. 85-142806w.
International Pharmaceutical Patents Co., Chem. Abst 89-24287n.
Ravizza S.p.A., Chem. Abst. 93-26426p.
Stampa, Chem. Abst. 97-182392n.
Dunwell et al., Chem. Abst. 83-97265q.
Dunwell et al., Chem. Abst. 82-118774b.
Evans, Chem. Abst. 80-70798s.
Duran et al., Chem. Abst. 98-160693e.
International Pharmaceutical Patents Co., Chem. Abst. 89-24287n.
Dunwell et al., J. Med. Chem. 1975, vol. 18, No. 1, 53-58.

Primary Examiner—Donald G. Daus
Assistant Examiner—Cecilia Shen
Attorney, Agent, or Firm—Stevens, Davis, Miller & Mosher

[57] ABSTRACT

A process for preparing 2(4-fluorophenyl)α-methyl-5-benzoxazole acetic acid starting from 4-hydroxy-3-amino-phenylacetic acid, which is firstly reacted with 4-fluorobenzoyl chloride, and the product obtained is reacted with phosphoric acid; the 2(4-fluorophenyl)5-benzoxazole acetic acid obtained in this manner is esterified with ethyl alcohol, and the ester is treated with diethyloxalate; the ethyl 2(4-fluorophenyl)5-benzoxazole oxalacetate obtained is reacted with formaldehyde and potassium carbonate to obtain ethyl 2(4-fluorophenyl)5-benzoxazole acrylate, which is hydrolysed to obtain the corresponding acid, from which the 2(4-fluorophenyl)α-methyl-5-benzoxazole acetic acid is obtained by hydrogenation.

6 Claims, No Drawings

PROCESS FOR PREPARING 2(4-FLUOROPHENYL)ALPHA-METHYL-5-BENZOXAZOLE ACETIC ACID

This invention relates to a new process for preparing 2(4-fluorophenyl)α-methyl-5-benzoxazole acetic acid.

In 2(4-fluorophenyl)α-methyl-5-benzoxazole acetic acid, of formula:

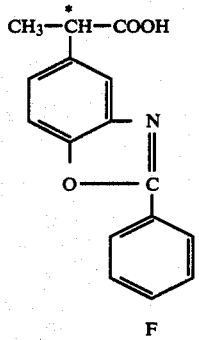

the carbon atom indicated by the asterisk is asymmetric, so that it exists in the dextrorotatory and levorotatory form in addition, obviously, to the raceme mixture form.

Compounds of the type indicated by the aforesaid formula are known (J. Medic. Chem. 1975, Vol. 18, No. 1, pages 53–58), and they are also known to be good anti-inflammatory agents, which are considerably more powerful than phenylbutazone, compared with which they also have the advantage of lower toxicity.

It is also known that the dextrorotatory form exerts a considerably greater anti-inflammatory activity than the levorotatory antipode, or than the corresponding raceme mixture.

The production of the dextrorotatory form with sufficient optical purity is therefore of considerable interest.

The preparation of (+)-2(4-fluorophenyl)α-methyl-5-benzoxazole acetic acid is known for example from British Pat. No. 1,495,488 and Italian Pat. No. 22454 A/82.

The applicant has also filed a patent application (Italian patent application No. 26498 A/78) for a process which enables 2(4-fluorophenyl)α-methyl-5-benzoxazole acetic acid to be prepared either in the form of the raceme mixture or in the form of individual optical antipodes, starting from (-)2-(4'-hydroxy-3'-nitrophenyl)-propionitrile.

We have now discovered the subject of the present invention, namely a decidedly improved process which enables 2(4-fluorophenyl)α-methyl-5-benzoxazole acetic acid to be produced with higher yields and under milder conditions than those of the known art, with considerable advantages with regard to its industrial preparation.

The process for preparing 2(4-fluorophenyl)α-methyl-5-benzoxazole acetic acid (I)

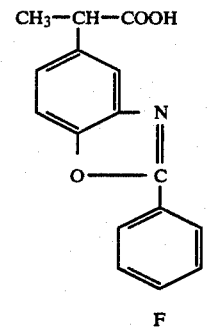

according to the present invention is characterised by comprising the following operational stages which are represented hereinafter by their respective chemical reactions:

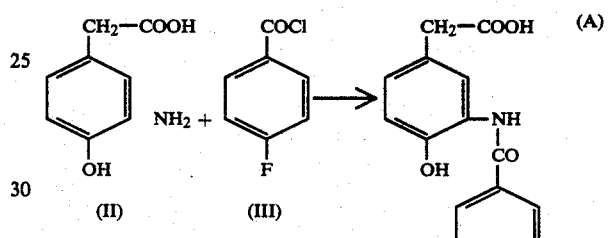

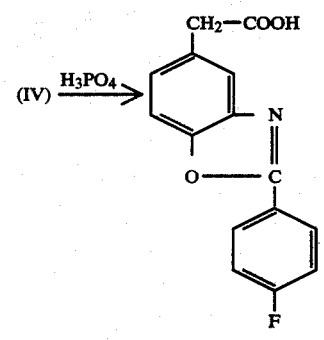

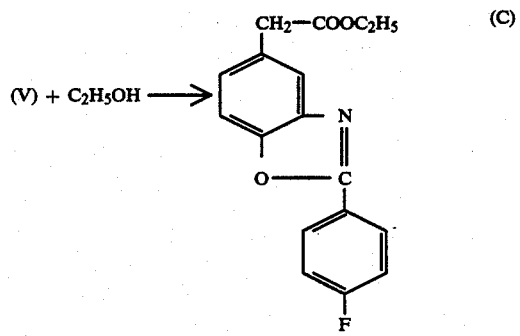

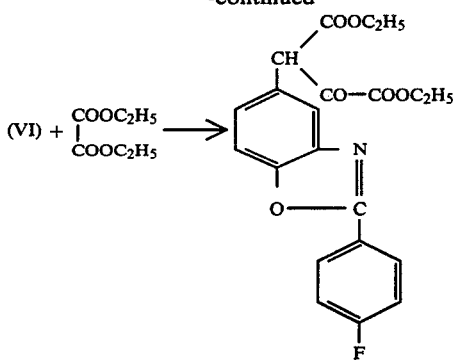

(VII)

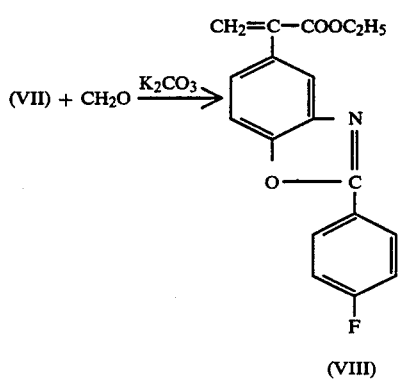

(VIII)

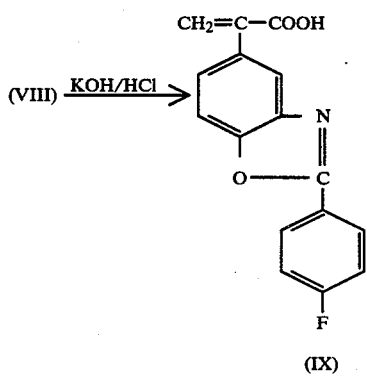

(IX)

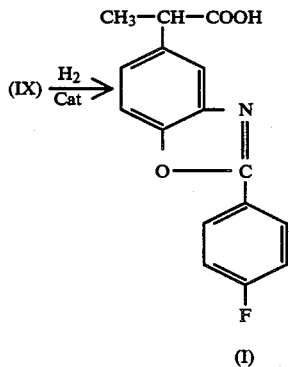

(I)

The characteristics of the process according to the present invention will be more apparent from the detailed description given hereinafter of a preferred method for implementing the invention, which is described for illustrative purposes.

In stage (A) 4-hydroxy-3-aminophenylacetic acid (II) is reacted with 4-fluorobenzoyl chloride (III) to produce 3(4-fluoro)-benzamido-4-hydroxyphenylacetic acid (IV). The reaction is conducted in a reaction medium constituted by a 2%–5% aqueous sodium bicarbonate solution operating at a temperature of between 0° and 30° C., for a time of between 3 and 6 hours.

The product (IV) is obtained with a yield of about 95%.

In stage (B), in which the heterocyclic ring is formed, the product (IV) is treated with a 70–80 weight % phosphoric acid solution at a temperature of 120°–125° C. for a time of between 30 minutes and 1 hour.

The mixture is allowed to cool, and the obtained 2(4-fluorophenyl)-5-benzoxazole acetic acid (V) is crystallised by adding water at a temperature of 25° C.

The product (V) is obtained with a yield of between 90% and 95%.

In stage (C) the product (V) is esterified by treatment with ethyl alcohol in the presence of $H_2SO_4$, by heating under reflux for some hours to obtain ethyl (4-fluorophenyl)5-benzoxazole acetate (VI) with a yield of 80%–85%.

In stage (D) the ester (VI) is reacted with diethyloxalate in the presence of sodium methylate in a reaction medium constituted by an ether or an hydrocarbon solvent. The mixture is heated to boiling under reflux for 20–30 hours and is then cooled and neutralised with a 5% $H_2SO_4$ solution. The organic phase is washed with a saturated NaCl solution and then with $H_2O$ and dried by treatment with $Na_2SO_4$, after which it is concentrated to a small volume to obtain ethyl 2(4-fluorophenyl)-5-benzoxazole oxalacetate (VII) with a yield of between 90% and 95%.

In stage (E) the product (VII) is treated with formaldehyde in an aqueous $K_2CO_3$ solution at ambient temperature under agitation, for a time of 4–6 hours. Ethyl 2(4-fluorophenyl)5-benzoxazole acrylate (VIII) is thus obtained, with a yield exceeding 95%.

In stage (F) the ester (VIII) is hydrolysed to obtain the corresponding acid by firstly treating it in a tetrahydrofuran solution with a KOH solution at ambient temperature for 20–30 hours and then acidifying with a solution of HCl in t-butylmethylether.

2(4-fluorophenyl)5-benzoxazole acrylic acid (IX) is thus obtained, with a yield of 90%–95%.

In stage (G) the product (IX) is hydrogenated under atmospheric pressure at a temperature of 25°–40° C., using 5% Pd-on-carbon as catalyst in a reaction medium constituted by ethyl alcohol. In this reaction, the hydrogenation leads to the formation of 2(4-fluorophenyl)α-methyl-5-benzoxazole acetic acid (I) with a practically quantitative yield.

The following example is given as a non-limiting illustration of the process for preparing -2(4-fluorophenyl)α-methyl-5-benzoxazole acetic acid.

EXAMPLE 1

Preparation of 3(4-fluoro)benzamido-4-hydroxyphenyl acetic acid 92.4 g of 4-hydroxy-3-nitrophenylacetic acid are suspended in a solution constituted by 785 ml of $H_2O$ and 21.2 g of $NaHCO_3$. 5 g of a catalyst constituted by 5% Pd-on-carbon are suspended in the solution, which is then hydrogenated at ambient temperature for 4 hours, to obtain 4-hydroxy-3-aminophenylacetic acid. The catalyst is separated by filtration in a nitrogen environment, and the aqueous solution is used for the reaction with 4-fluorobenzoyl chloride, which is carried out in the following manner: the aqueous solution is cooled to 5° C. in a nitrogen environment, 460 ml of t-butylmethylether are added, and then 74 ml of 4-fluorobenzoyl chloride dissolved in 170 ml of t-butylmethylether are fed slowly.

The mixture is agitated vigorously for 6 hours at ambient temperature, after which it is filtered to recover the product. A further small quantity of product is recovered from the mother liquors by evaporating the solvent.

A total of 127 g of 3(4-fluoro)benzamido-4-hydroxyphenylacetic acid are obtained with a yield of 94%.

The product had a melting point of 225°-230° C., and was analysed by TLC (benzene:dioxane:acetic acid=90:25:4).

Preparation of 2(4-fluorophenyl)5-benzoxazole acetic acid 127 g of finely ground 3(4-fluoro)benzamido-4-phenylacetic acid are added to 1 liter of a 75 weight % phosphoric acid solution heated to 130° C. and under agitation. The heating is continued to 125° C. for 30 minutes to obtain complete dissolving, after which the solution is cooled to 50° C. and water is slowly added until the product crystallises. Further water is added to form a total quantity of 3 liters, and agitation is continued for 2 hours. The mixture is filtered, the solid is pulped in distilled water, refiltered and dried.

110 g of crude product are obtained, and cristallised from ethanol to obtain 95 g of crystallised product with a yield of 80%.

The product has a melting point of 194°-196° C. and is analysed by TLC (benzene:dioxane:acetic acid=90:25:4).

Preparation of ethyl(4-fluorophenyl)5-benzoxazole acetate 85 grams of 2(4-fluorophenyl)5-benzoxazole acetic acid are treated with 300 ml of ethyl alcohol and 4.7 ml of $H_2SO_4$ and boiled under reflux for 3 hours.

The mixture is concentrated under vacuum, cooled to 25° C. and filtered to obtain 78 g of product with a yield of 83%.

The product has a melting point of 123°-124° C. and is analysed by TLC (benzene:ethyl acetate=10:1).

Preparation of ethyl 2(4-fluorophenyl)5-benzoxazole oxalacetate 68 grams of ethyl 2(4-fluorophenyl)5-benzoxazole acetate are suspended in 890 ml of toluene, after which 210 ml of toluene-ether containing 15.36 g of sodium methylate and 51.54 ml of diethyloxalate are added.

The resultant mixture is heated to boiling under reflux for 24 hours, and is then cooled and neutralised with 5% sulphuric acid.

The organic phase is washed firstly with a saturated sodium chloride solution and then with water, and is finally dried by treatment with sodium sulphate.

86 g of product are obtained with a yield of 91%.

The product has a melting point of 118°-120° C. and is analysed by TLC (benzene:ethyl acetate=10:1).

Preparation of ethyl 2(4-fluorophenyl)5-benzoxazole acrylate 86 grams of ethyl 2(4-fluorophenyl)5-benzoxazole oxalacetate are suspended in 232 ml of 20% formaldehyde, and a solution of 63 g of $K_2CO_3$ in 390 ml of water is added.

The mixture is agitated for 5 hours at ambient temperature and is then extracted with t-butylmethylether.

The organic phase is washed with water, dried with $Na_2SO_4$, and the solvent then evaporated.

59 g of product are obtained with a yield of 97%.

The product has a melting point of 98°-100° C. and is analysed by TLC (benzene:ethyl acetate=10:1).

Preparation of 2(4-fluorophenyl)5-benzoxazole acrylic acid 59 grams of ethyl 2(4-fluorophenyl)5-benzoxazole acrylate are dissolved in 425 ml of tetrahydrofuran, 850 ml of a 3% KOH solution are added, and the mixture kept under agitation at ambient temperature for 24 hours.

The solution is partly evaporated under vacuum at 40° C., cooled to ambient temperature, 500 ml of t-butylmethylether are added, and the mixture acidified with dilute (1:10) HCl to pH 2.

The ether phase is separated, and the aqueous phase is extracted twice with ether. The pooled ether solution is dried and evaporated.

The residue is taken up in diisopropylether.

50 g of product are obtained with a yield of 93%.

The product has a melting point of 237°-240° C. and is analysed by TLC (benzene:dioxane:acetic acid=90:25:4).

Preparation of 2(4-fluorophenyl)α-methyl-5-benzoxazole acetic acid 50 grams of 2(4-fluorophenyl)5-benzoxazole acrylic acid in 500 ml of ethyl alcohol are hydrogenated under atmospheric pressure and 35° C. in the presence of 5 g of catalyst constituted by 5% Pd-on-carbon for 3 hours.

The catalyst is separated by filtration, and the solution is concentrated to a small volume.

50 g of product are obtained with a yield of 99%.

The product has a melting point of 164°-165° C. and is analysed by TLC (benzene:dioxane:acetic acid=90:25:4).

We claim:

1. A process for preparing 2(4-fluorophenyl)α-methyl-5-benzoxazole acetic acid, characterised in that 4-hydroxy-3-aminophenylacetic acid is firstly reacted with 4-fluorobenzoyl chloride, and the product obtained is reacted with phosphoric acid;
   the 2(4-fluorophenyl)5-benzoxazole acetic acid obtained in this manner is esterified with ethyl alcohol and the ester is treated with diethyloxalate;
   the ethyl 2(4-fluorophenyl)5-benzoxazole oxalacetate obtained is reacted with formaldehyde and potassium carbonate to obtain ethyl 2(4-fluorophenyl)5-benzoxazole acrylate, which is hydrolysed to obtain the corresponding acid, from which 2(4-fluorophenyl)α-methyl-5-benzoxazole acetic acid is obtained by hydrogenation.

2. A process as claimed in claim 1, characterised in that said reaction between 4-hydroxy-3-aminophenylacetic acid and 4-fluorobenzoyl chloride is conducted in a reaction medium constituted by an aqueous sodium bicarbonate solution of between 2% and 5% strength, operating at a temperature of between 0° and 30° C. for a time of between 3 and 6 hours, and the product thus obtained is treated with a 70–80 weight % $H_3PO_4$ solution at a temperature of 120°–125° C. for a time of between 30 minutes and 1 hour.

3. A process as claimed in claim 1, characterised in that said esterification of 2(4-fluorophenyl)5-benzoxazole acetic acid is conducted in the presence of $H_2SO_4$ at boiling point under reflux for some hours, and said treatment of the ester with diethyloxalate is conducted in the presence of sodium methylate in a reaction medium constituted by an ether or an hydrocarbon solvent at boiling point under reflux for 20–30 hours.

4. A process as claimed in claim 1, characterised in that said reaction between ethyl 2(4-fluorophenyl)5-benzoxazole oxalacetate and formaldehyde and potassium carbonate is conducted in an aqueous solution at ambient temperature for a time of 4–6 hours.

5. A process as claimed in claim 1, characterised in that said hydrolysis of ethyl 2(4-fluorophenyl)5-benzoxazole acrylate is conducted by treatment with KOH in a tetrahydrofuran environment at ambient temperature for 20–30 hours, followed by acidification with HCl in t-butylmethylether.

6. A process as claimed in claim 1 characterised in that said hydrogenation of 2(4-fluorophenyl)5-benzoxazole acrylic acid is conducted under atmospheric pressure at a temperature of 25°–40° C. using a catalyst in the form of 5% Pd-on-carbon, in a reaction medium constituted by ethyl ether.

* * * * *